(12) United States Patent
Urban et al.

(10) Patent No.: US 10,172,773 B2
(45) Date of Patent: *Jan. 8, 2019

(54) USE OF CHARGED SURFACTANTS FOR REDUCING TEXTILE STAINING BY ANTIPERSPIRANTS

(71) Applicants: Michael Urban, Hamburg (DE); Heike Miertsch, Hamburg (DE); Stefan Biel, Hamburg (DE); Sabine Kuehne, Langenfeld (DE); Stefan Bruening, Duesseldorf (DE); Rolf Kawa, Monheim (DE)

(72) Inventors: Michael Urban, Hamburg (DE); Heike Miertsch, Hamburg (DE); Stefan Biel, Hamburg (DE); Sabine Kuehne, Langenfeld (DE); Stefan Bruening, Duesseldorf (DE); Rolf Kawa, Monheim (DE)

(73) Assignee: Beiersdorf AG, Hamburg (DE)

( * ) Notice: Subject to any disclaimer, the term of this patent is extended or adjusted under 35 U.S.C. 154(b) by 216 days.

This patent is subject to a terminal disclaimer.

(21) Appl. No.: 14/073,308

(22) Filed: Nov. 6, 2013

(65) Prior Publication Data

US 2014/0093463 A1   Apr. 3, 2014

Related U.S. Application Data

(62) Division of application No. 13/203,588, filed as application No. PCT/EP2010/001132 on Feb. 24, 2010, now Pat. No. 8,691,250.

(30) Foreign Application Priority Data

Feb. 27, 2009  (DE) .................. 10 2009 010 665

(51) Int. Cl.
```
A61K 8/41    (2006.01)
A61Q 15/00   (2006.01)
A61K 8/42    (2006.01)
A61K 8/26    (2006.01)
A61K 8/28    (2006.01)
A61K 8/86    (2006.01)
D06F 35/00   (2006.01)
A61K 8/37    (2006.01)
```

(52) U.S. Cl.
CPC .................. *A61K 8/42* (2013.01); *A61K 8/26* (2013.01); *A61K 8/28* (2013.01); *A61K 8/37* (2013.01); *A61K 8/416* (2013.01); *A61K 8/86* (2013.01); *A61Q 15/00* (2013.01); *D06F 35/005* (2013.01)

(58) Field of Classification Search
None
See application file for complete search history.

(56) References Cited

U.S. PATENT DOCUMENTS

| | | | |
|---|---|---|---|
| 3,934,004 A | 1/1976 | Orren | |
| 3,949,066 A | 4/1976 | Clark | |
| 4,027,007 A * | 5/1977 | Messina | ............ A61K 8/19 424/46 |
| 4,110,428 A | 8/1978 | Kuhn et al. | |
| 4,268,499 A * | 5/1981 | Keil | ............ A61K 8/06 424/47 |
| 4,477,431 A | 10/1984 | Suffis et al. | |
| 5,547,661 A | 8/1996 | Sun et al. | |
| 5,593,663 A | 1/1997 | Leng et al. | |
| 5,593,779 A * | 1/1997 | Mori | ............ C12N 11/08 428/375 |
| 5,733,534 A | 3/1998 | Sawin et al. | |
| 5,833,965 A | 11/1998 | Sun et al. | |
| 5,916,546 A | 6/1999 | Sawin et al. | |
| 5,972,319 A * | 10/1999 | Linn | ............ A61K 8/0229 424/401 |
| 5,997,850 A | 12/1999 | Tang et al. | |
| 6,066,314 A | 5/2000 | Tang et al. | |
| 6,790,435 B1 * | 9/2004 | Ma | ............ A61K 8/0208 424/400 |
| 7,196,117 B2 | 3/2007 | Beltran et al. | |
| 2004/0254232 A1 | 12/2004 | Beltran et al. | |
| 2006/0063246 A1 | 3/2006 | Paloheimo et al. | |
| 2006/0281652 A1 | 12/2006 | Keenan et al. | |
| 2008/0070986 A1 * | 3/2008 | Mehling | ............ A61K 8/39 514/558 |
| 2008/0108709 A1 | 5/2008 | Meyer et al. | |

FOREIGN PATENT DOCUMENTS

| | | |
|---|---|---|
| CA | 2373513 A1 | 11/2000 |
| DE | 10057767 A1 | 5/2002 |
| DE | 10163247 A1 | 7/2003 |
| DE | 10309180 A1 | 6/2004 |
| DE | 10321138 A1 | 11/2004 |
| DE | 10322059 A1 | 12/2004 |
| DE | 101005029386 A1 | 1/2007 |
| DE | 102006037113 A1 | 2/2008 |
| DE | 102007028508 A1 | 4/2008 |

(Continued)

*Primary Examiner* — Nissa M Westerberg
(74) *Attorney, Agent, or Firm* — Abel Law Group, LLP

(57) ABSTRACT

Disclosed is a method of reducing or avoiding staining in or on clothing caused by a cosmetic or dermatological preparation comprising one or more antiperspirant substances and/or of improving the ability of stains in or on clothing which are caused at least in part by said preparation to be washed out from the clothing. The method comprises including in the preparation one or more cationic surfactants.

18 Claims, 1 Drawing Sheet

(56) References Cited

FOREIGN PATENT DOCUMENTS

| | | | |
|---|---|---|---|
| DE | 102008052748 A1 | 4/2010 | |
| EP | 0676193 A2 | 10/1995 | |
| EP | 1027880 A2 | 8/2000 | |
| EP | 2082724 A1 | 7/2009 | |
| GB | 1300260 | 12/1972 | |
| GB | 1409533 | 10/1975 | |
| WO | 9716163 A1 | 5/1997 | |
| WO | 9843605 A1 | 10/1998 | |
| WO | 0067703 A2 | 11/2000 | |
| WO | 0067713 A1 | 11/2000 | |
| WO | 0124766 A1 | 4/2001 | |
| WO | 03053388 A1 | 7/2003 | |
| WO | WO 2008133809 A1 * | 11/2008 | ............. A61K 8/362 |

* cited by examiner

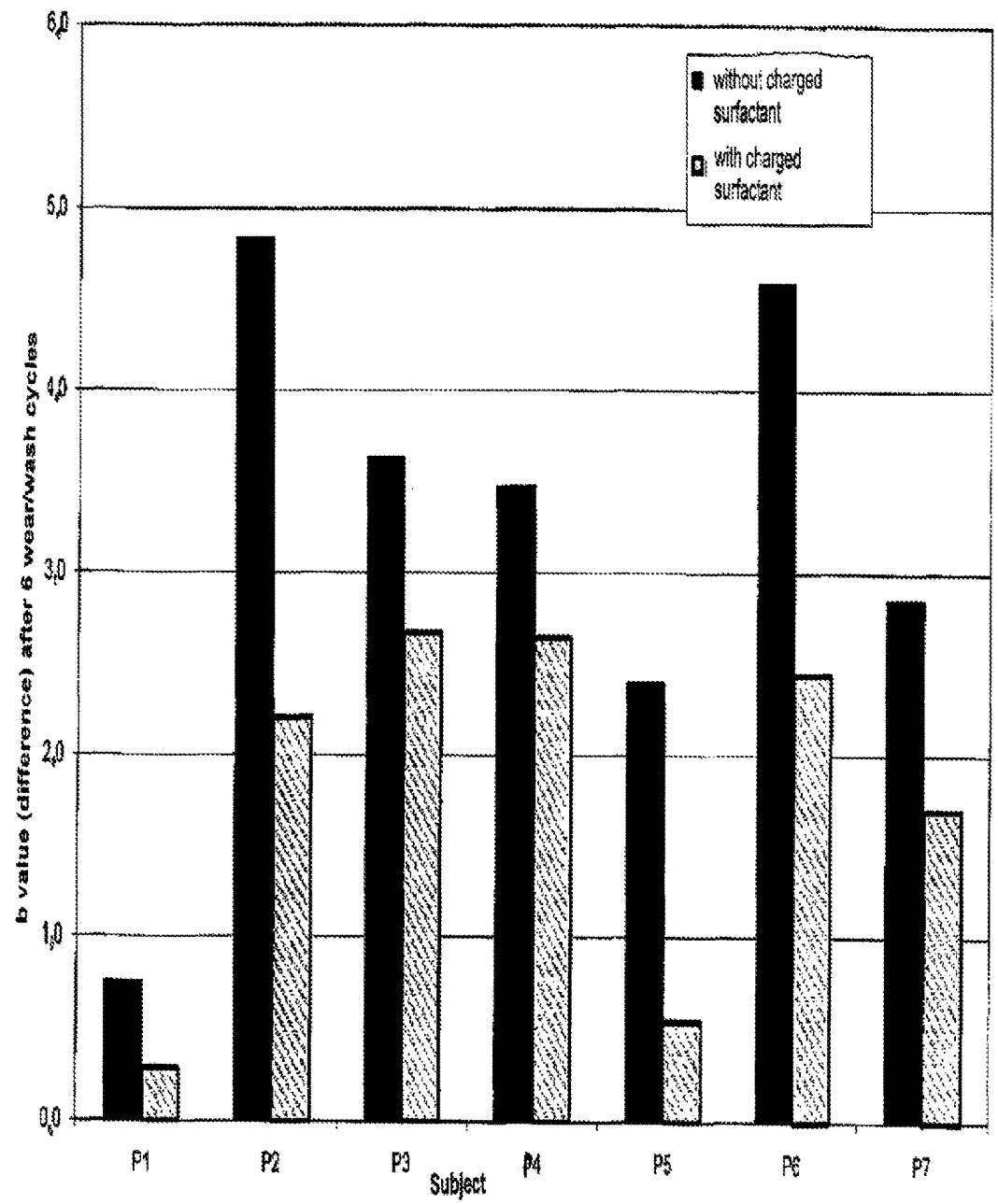

USE OF CHARGED SURFACTANTS FOR REDUCING TEXTILE STAINING BY ANTIPERSPIRANTS

CROSS-REFERENCE TO RELATED APPLICATIONS

The present application is a divisional of U.S. application Ser. No. 11/203,588, which is a National Stage of International Application Number PCT/EP2010/001132, filed on Feb. 24, 2010; the entire disclosures of these applications are expressly incorporated by reference herein.

BACKGROUND OF THE INVENTION

1. Field of the Invention

The invention comprises the use of charged surfactants in preparations with an antiperspirant effect for reducing staining in or on clothing and improving the ability of stains to be washed out of clothing.

2. Discussion of Background Information

With the use of antiperspirants or deodorants, many consumers complain about undesirable stains in the underarm area in clothing. These are frequently yellowish stains which can also tend to become incrusted. These deposits and stains are produced above all due to a complex interaction between product, skin fat, sweat and detergent and are often difficult to remove with conventional washing methods.

The stains can be pronounced to different extents, depending on the person. One cause is the aluminum salts used in most deodorant antiperspirant products, which act as antiperspirant active substances. These stubborn stains often cannot be completely removed or can be completely removed only with difficulty by washing, even with pretreatment with stain removers.

There are numerous literature and patents that deal with soiling on the skin and clothing and the avoidance thereof in the case of the use of antiperspirants.

EP 1178775 describes the use of water-soluble surfactants to improve the ability of washing out the residue from the skin and clothing. Combinations of astringent salts with water-soluble, nonionic surfactants are described, which are to have a rapid start of antiperspirant effect and a high effectiveness.

EP 973492 A1 describes the use of surface-active substances, chiefly nonionic emulsifiers, in antiperspirants. The antiperspirant stick formulations comprise nonvolatile emollients, a vehicle, e.g., cyclomethicone, a fatty alcohol, such as stearyl alcohol, an antiperspirant agent and a surfactant. The problem of the formation of white residue on the skin and clothing, which can form with the use of aluminum-containing antiperspirants, is described. The problem is addressed herein of the whitening effect of the formulation by an adjustment of the refractive index of the constituents.

EP 858317 A1 describes preparations with surface active substances with an HLB>10 to remove the fatty residue on the skin.

EP 696188 A1 describes the use of a wash-off agent for removing the lipid components from the skin, preferably ethoxylates are used for this purpose DE 102008052748, an earlier application of the patentee, describes that in anhydrous suspensions emulsifiers are used to improve the ability of the formulation to be washed off the skin. The structurants advantageously contained in the anhydrous formula can leave perceptibly waxy residues on the skin. Through the presence of polar groups on the emulsifiers used, the affinity to water is increased when the formulation is washed off and the residue disappears. Preferably nonionic emulsifiers are suitable for this purpose.

It is desirable to provide cosmetic antiperspirants that have a reduced soiling of clothing and above all that help to increase the ability to subsequently wash out the soiling.

In addition, these cosmetic preparations must not have any instabilities and should be easy to formulate.

An important aspect in the formulation of cosmetic antiperspirants is the good skin tolerance, so that in addition to the object of avoiding staining or improved washability, the skin tolerance must also be taken into consideration.

Furthermore, detergent surfactants are known, such as for example cationic surfactants, in particular quaternary ammonium compounds. A detergent surfactant is found in detergents, dishwashing detergents, shampoos, shower gels and designates the portion of the formulation that influences the washing or cleaning performance. Detergent surfactants increase the "solubility" of fat and dirt particles in water, which adhere to the laundry or the body. They can be of natural or synthetic origin. They are distinguished according to the type of load into anionic, cationic, amphoteric or nonionic.

DE 10322059 A1 describes hair-care products with styling properties, which comprise quaternary ammonium compounds as cationic surfactant.

DE 102007028508 describes detergent surfactant substances for improved ability to wash out the cosmetic agent from the skin. Quaternary ammonium compounds are thereby also considered to be an antimicrobial active substance and conditioning agent or softener.

In DE 102005029386 active substance combinations of glycopyrronium bromide and one or more hydrocolloids, which furthermore can contain cationic surfactants, are described.

DE 10321138 discloses biphasic antiperspirant products, wherein the oil phase contains, inter alia, a nonionic, cationic, zwitterionic or amphoteric emulsifier.

In DE 10309180 quaternary ammonium compounds are used in skin and hair treatments for personal hygiene as a cationic surfactant.

DE 102006037113 discloses cosmetic hair treatments with anti-dandruff agents, wherein, among other things, laureth-7 citrate as well as further cationic surfactants can be included. Antiperspirants are not disclosed.

U.S. Pat. No. 4,477,431 discloses a flowable, anhydrous preparation with 35-70% by weight powder, 1-20% by weight thickener, 19-45% by weight oil and 1-10% by weight surfactants, which can be nonionic and/or cationic.

EP 2082724 discloses an antimicrobial system with a cationic surfactant, which represents an ethyl ester of the lauramide of arginine hydrochloride (LAE).

EP 1183003 discloses an antiperspirant preparation with fine particles of aluminum, zirconium, or zinc salts, wherein the particles are impregnated with or encased by a water-soluble nonionic, zwitterionic or cationic surfactant.

EP 676193 discloses a preparation with an active substance, a "borate crosslinker", a surfactant and water. The active substance can be, inter alia, an aluminum salt, and the surfactant is preferably nonionic. The surfactants prevent the product from becoming hard and brittle.

EP 10163247 discloses the foam application of a deodorant or antiperspirant active substance from a foam dispenser (pump or propellant gas) of a liquid, foaming surfactant solution which consists of water, at least one foaming surfactant, oil, perfume, at least one nonionic solubilizer for the perfume and a deodorant or antiperspirant active agent.

The hair conditioner sold under the trade name VARI-SOFT® PATC by Degussa (Evonik) lists as one of the outstanding properties the reduction of the washing out of chemical hair dyes with the use of shampoos. That is, the dye is expected to remain longer in the hair when VARI-SOFT® PATC is used.

SUMMARY OF THE INVENTION

The invention comprises preparations with antiperspirant effect comprising one or more charged surfactants.

Cosmetic as well as dermatological formulations are suitable as preparations.

The preparations comprising one or more charged surfactants reduce or avoid soiling in or on clothing and improve the ability to wash out stains from clothing that are also caused by the preparation itself.

BRIEF DESCRIPTION OF THE DRAWINGS

In the accompanying drawings, FIG. 1 is a graph illustrating the difference in the b value (yellow) of the CIE L*a*b color space after 6 wear and wash cycles on clothing worn by 7 individual test subjects that had applied formulations containing antiperspirant substances with and without charged surfactant.

DETAILED DESCRIPTION OF THE INVENTION

Preferably, the weigh ratio of antiperspirant to surfactant is selected in the range of 1:1 to 30:1, preferably 2:1 to 20:1, very particularly preferably 3:1 to 8:1. If at least one cationic as well as at least one anionic surfactant are contained as charged surfactants according to the invention, the weigh ratio between cationic and anionic surfactants is advantageously 10:1 to 1:3, preferably 6:1 to 1:2.

Thus in particular the use of one or more charged surfactants in cosmetic or dermatological preparations comprising one or more substances with antiperspirant effect for reducing or avoiding staining of clothing caused by the preparation and for improving the ability to wash out these stains, is according to the invention. These are primarily preparations comprising one or more antiperspirants, in particular those based on aluminum.

The reduction or avoidance of soiling of textiles before and in particular after washing means according to the invention the reduced b value, which is determined photometrically by means of the colorimetric measures in the CIE L*,a*,b color space and which is measured compared to the b values of the textile stained with a preparation with antiperspirant agent but without surfactants according to the invention.

It has been shown by a panel test that the staining by the preparation according to the invention in or on clothing is basically reduced or the clothing is stained less in a yellowish manner. This is explained below.

In order to suppress the odor of sweat for a longer period, the use of cosmetic preparations is indispensible. Conventional cosmetic deodorants are based on different principles of action, which can also be combined: on the one hand deodorant active substances are used which suppress the growth of the bacteria causing the sweat odor. These germ inhibiting (bacteriostatic) agents include for example triclosane, chlorhexidine or the naturally occurring compounds such as farnesol and phenoxyethanol.

On the other hand, antiperspirants are used, which prevent sweat secretion by blocking the sweat gland outlets. In by far the most antiperspirants, the formation of sweat can be reduced through astringents—primarily aluminum salts such as aluminum hydroxychloride (aluminum chlorohydrate) or aluminum/zirconium salts.

The combination of astringents with antimicrobially active substances in one and the same composition is also customary. Furthermore, perfumes are used to cover the smell of sweat.

Known are further compounds having an antiperspirant effect, such as 4-[(2-cyclopentyl-2-hydroxyphenylacetyl) oxy]-1,1-dimethylpiperidinium bromide.

In addition to liquid deodorants such as spray and roll-on, solid preparations, for example deodorant sticks ("sticks"), powders, powder sprays, personal hygiene cleansing compositions etc. are known and customary.

As antiperspirant active ingredient it is advantageously possible to incorporate activated acidic aluminum and/or aluminum/zirconium salts in aqueous solution. Here, the concentration ranges described refer to the so-called active contents of the antiperspirant complexes: in the case of the aluminum compounds, to anhydrous complexes, in the case of the aluminum/zirconium compounds, to anhydrous and buffer-free complexes glycine is generally used as buffer here).

The following list of antiperspirant active ingredients which are to be used advantageously is in no way intended to be limiting:

aluminum salts (of the empirical formula $[Al_2(OH)_mCl_n]$, wherein m+n=6):

aluminum chlorohydrate $[Al_2(OH)_5Cl]*H_2O$

Standard Al complexes: Locron L, Locron LIC, Locron LIF (Clariant), Chlorhydrol (Reheis), ACH-303 (Summit), Aloxicoll L (Giulini).

Activated Al complexes: Reach 501 (Reheis), Aloxicoll 51 L aluminum sesquichlorohydrate $[Al_2(OH)_{4.5}Cl_{1.5}]*H_2O$ Standard Al complexes: Aloxicoll 31 L (Giulini), Westchlor 186 (Westwood Chemicals)

Activated Al complexes: Reach 301 (Reheis)

aluminum dichlorohydrate $[Al_2(OH)_4Cl_2]*H_2O$

Aluminum zirconium salts:

Aluminum/zirconium trichlorhydrex glycine $(Al_4Zr(OH)_{13}Cl_3)\times H_2O\times Gly$ Standard Al/Zr complexes: Rezal 33GC (Reheis), AZG-7164 (Summit)

Aluminum/zirconium tetrachlorhydrex glycine (GLY) $[Al_4Zr(OH)_{12}O_4]\times H_2O\times Gly$ Standard Al/Zr complexes: Rezal 36, Rezal 36G, Rezal 36 GC (Reheis), AZG-368 (Summit), Zirkonal L435G (Giulini), Westchlor ZR 35 BX5, Westchlor ZR 41 (Westwood Chemicals)

Aluminum/zirconium pentachlorhydrex glycine $[Al_8Zr(OH)_{23}Cl_5]\times H_2O\times Gly$ Standard Al/Zr complexes: Rezal 67 (Reheis), Zirkonal L540, Zirkonal L530 PG (Giulini), Westchlor ZR 80B (Westwood Chemicals)

Aluminum/zirconium octachlorhydrex glycine $[Al_8Zr(OH)_{20}Cl_8]\times H_2O\times Gly$: Westchlor ZR 82B Reach AZP—908 SUF activated aluminum zirconium tetrachlorohydrex Gl Reach AZZ—902 SUF activated aluminum zirconium trichlorohydrex Glyc However, buffer-free aluminum/zirconium salts can also be likewise used advantageously.

The antiperspirant active substances from the group described above of the astringent antiperspirant agents, the classic antiperspirant agents, are used in the formulations according to the invention in a quantity of 0.05 to 40% by weight, preferably 0.1 to 20% by weight, based on the total mass of the preparation, i.e., including any propellant gases present.

As previously stated, a disadvantage of the use of antiperspirants, in particular aluminum salts, is the formation of residue in or on clothing, which can stain clothing in an unattractive manner.

Textile staining means stains, in particular in the underarm region. These are stains that remain in clothing after wearing and/or washing and can become more intensive with increasing age of the article of clothing. These stains are not to be understood to mean the residue on the skin or clothing referred to as "whitening."

Instead, according to the invention this relates to mostly yellowish stains, which are produced when the cosmetic product or constituents thereof reach the textiles during sweating together with the armpit secretions. Part of these deposits are washed out during washing, another part remains on the textile as residue.

According to the invention, the preparation cannot reduce or prevent the formation of any stains which can form on an article of clothing for many reasons. However, the preparation according to the invention can reduce or prevent the formation of those stains that are produced by the preparation itself, in particular those due to antiperspirant substances, and can improve the ability for them to be washed out.

As a gauge of the improvement or reduction thereby the difference from the staining or the washing out thereof in the use of the preparation according to the invention and the preparation without charged surfactants is defined.

However, in principle independent observers (panel) also judge that the stains of the preparations according to the invention do not occur on the clothing at all or at least appear to be less yellowish. This constitutes a basic reduction of staining.

Stains that are produced as white stains in the case of direct contact of a deodorant or antiperspirant with the fabric are not meant according to the invention. These are rather whitish deposits of the formula constituents, e.g., aluminum salts. These stains can be easily avoided if the product is given a chance to dry before the clothing is put on. This white residue can generally be removed mechanically (brushing) or by washing. The problem of "whitening" is discussed in detail in the prior art and approaches to a solution are provided there.

According to the invention it is in particular a matter of the known yellowish stains from antiperspirants in or on clothing, after the article of clothing has been washed. According to the invention the solution concept of the improved ability to be washed out also starts here. The yellow value of the stain is therefore defined in particular by the b value, which can be determined photometrically by means of the colorimetric measures in the CIE L*a*b color space. Preferably, the use of the stain avoidance or improved washability relates to textiles that contain cotton or consist of cotton.

According to the invention, one or more charged surfactants are added to the cosmetic preparations for this purpose.

Surfactants are substances that lower the surface tension of a liquid or the interfacial tension between two phases and render possible or support the formation of dispersions. Surfactants make it possible that two liquids that actually cannot be mixed with one another, such as oil and water, can be dispersed.

Furthermore, surfactants are described as amphiphilic substances which can dissolve organic, nonpolar substances in water. Due to their specific molecular structure with at least one hydrophilic and one hydrophobic part of the molecule they ensure a lowering of the surface tension of water, wetting of the skin, the facilitation of dirt removal and dissolution, easy rinsing and, as desired, foam regulation.

The hydrophilic portions of a surfactant molecule are usually polar functional groups, for example $-COO^-$, $-OSO_3^{2-}$, $-SO_3^-$, while the hydrophobic parts as a rule are nonpolar hydrocarbon residues. Surfactants are generally classified according to the type and charge of the hydrophilic part of the molecule. A distinction can be made here among four groups:

Anionic surfactants
Cationic surfactants
Amphoteric surfactants and
Nonionic surfactants.

Anionic surfactants have as functional groups generally carboxylate, sulfate or sulfonate groups. In aqueous solution they form negatively charged organic ions in acidic or neutral media. Cationic surfactants are characterized almost exclusively by the presence of a quaternary ammonium group. In aqueous solution they form positively charged ions in acidic or neutral media. Amphoteric surfactants contain anionic as well as cationic groups and accordingly behave in aqueous solution depending on the pH value like anionic or cationic surfactants. In strongly acidic media they have a positive charge and in alkaline media a negative charge.

Polyether chains are typical of nonionic surfactants. Nonionic emulsifiers are understood to be surface-active substances which do not form ions in aqueous solution. The hydrophilicity of such nonionic emulsifiers is achieved through the proportion of the polar groups in the molecule. The nonionic emulsifiers include fatty alcohols (e.g., cetyl alcohol or stearyl alcohol), partial fatty acid esters of polyhydric alcohols with saturated fatty acids (e.g., glycerol monostearate), partial fatty acid esters of polyhydric alcohols with unsaturated fatty acids (e.g., glycerol monooleate, pentaerythritol monooleate), furthermore polyoxyethylene esters of fatty acids (e.g., polyoxyethylene stearate), polymerization products of ethylene oxide and propylene oxide on fatty alcohols (fatty alcohol polyglycol ethers) or fatty acids (fatty acid ethoxylates).

Nonionic surfactants or emulsifiers according to the invention are not included among charged surfactants.

According to the invention surfactants that act as emulsifier in the formula are not to be understood as charged surfactants either.

Surfactants as emulsifiers make it possible for two liquids that cannot be mixed with one another (for example, oil in water) to mix to form an emulsion. Due to the amphiphilic nature, they penetrate into the oil with their fat-soluble part. Through the hydrophilic part, the oil droplet now formed can be dispersed into the aqueous surroundings. Emulsifiers do not primarily have a detergent surfactant nature.

According to the invention, the nonionic surfactants or emulsifiers are thus not to be included by the term of charged surfactants.

It has now surprisingly been found that charged surfactants, i.e., anionic, cationic or amphoteric surfactants, preferably cationic and/or anionic surfactants, preferably quaternary ammonium compounds, so-called quats, in cosmetic preparations lead to a significant reduction in stains, which otherwise would usually be produced in the clothing by the cosmetic product.

Palmitamidopropyltrimonium chloride, trade name Varisoft® PATC, is used as a preferred quaternary ammonium compound.

Varisoft® PATC is composed of 60% palmitamidopropyltrimonium chloride in 40% propylene glycol as solvent. Alternatively, a mixture of palmitamidopropyltrimonium chloride and a fatty alcohol (cetearyl alcohol) can be used, trade name Tego Care CE 40.

In addition to quaternary ammonium compounds, the quats, further preferably anionic surfactants, preferably based on carboxylic acids and derivatives thereof, such as carboxylic acid esters, are also used as charged surfactant according to the invention, in particular ethoxylated carboxylic acid esters, very particularly here laureth-7 citrate.

Quaternary ammonium compound is the name for organic ammonium compounds with quaternary nitrogen atoms. They are produced by the conversion of tertiary amines with alkylation agents, such as, e.g., methyl chloride, benzyl chloride, dimethyl sulfate, dodecyl bromide, as well as ethylene oxide. Depending on the tertiary amine used, a distinction is made into three groups:

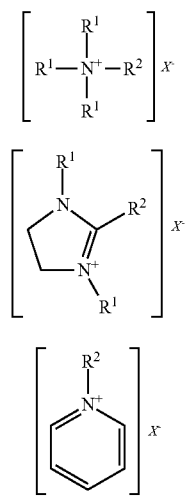

Where: $R^1=CH_3$, $R^2=C_{8-18}$, X=halogen
a) Linear alkyl ammonium compounds, b) imidazolinium compounds, c) pyridinium compounds
Formulations according to the invention advantageously contain at least one compound having the formula (I)

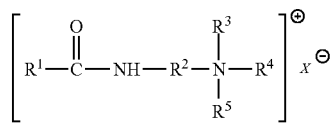

R1 represents a saturated or unsaturated linear branched or cyclic alkyl or aryl group having 8 to 24 C atoms,
R2 represents a saturated or unsaturated, linear, branched, or cyclic substituted or non-substituted alkylene group having 1 to 10 C atoms and 0 to 5 hydroxy groups
R3, R4, R5 independently of one another represent hydrogen, a C1-C4 alkyl group, a C5 or C6 cycloalkyl group, an aryl group or a C2-C4 hydroxyalkyl group, and X represents a monovalent anion.

Those compounds according to formula (I) are preferred according to the invention in which the radical R1 represents a saturated, linear C10-C18 alkyl group.

Those compounds according to formula (I) are also preferred according to the invention in which the radical R2 represents the group —CH2CH2CH2-.

Furthermore, those compounds according to formula (I) are also preferred in which the radicals R3, R4 and R5 each represent alkyl groups, for example, methyl, ethyl, propyl, isopropyl and butyl groups. In particular methyl groups are preferred.

Those compounds according to formula (I) are preferred in which the monovalent anion X represents halide, for example chloride or bromide or one of the two groups CH3-O—SO3 (methosulfate) or CH3CH2-O—SO3 (ethosulfate).

Linear alkyl ammonium compounds are preferred according to the invention. Preferred quaternary ammonium compounds are ammonium halides, in particular chlorides and bromides.

The quaternary ammonium compounds according to the invention do not include polymeric quaternary ammonium compounds, since they can lead to an intensification of the stains.

Furthermore, the polymers cannot be referred to as charged surfactants.

In particular preferred compounds according to formula (I) for the purposes of the invention are palmitamidopropyltrimonium chloride, as is commercially available for example under the trade name Varisoft® PATC from Evonik, behenamidopropyl ethyldimonium ethosulfate, such as is commercially available for example under the trade name Mackernium BAPDES from McIntyre, stearamidopropyl trimonium methosulfate, as is commercially available for example under the trade name Catigene SA-70 from Stepan Company and/or undecylamidopropyltrimonium methosulfate, such as is available for example under the trade name Rewocid UTM 185 from Evonik.

Laureth-7 citrate is a preferred anionic surfactant. Laureth-7 citrate can be obtained as PLANTAPON LC 7 (Cognis). It is an anionic surfactant, an ester of laureth-7 and citric acid.

The charged surfactants, in particular quaternary ammonium compounds are advantageously used in a proportion of 0.1 to 5% by weight, preferably 0.5 to 3% by weight of active content, i.e., without solvent such as propylene glycol, based on the total mass of the preparation.

It has surprisingly proven that in particular a certain weight ratio of antiperspirant agent, in particular aluminum salts, to charged surfactant contributes to a significant reduction in stains or to their ability to be washed out.

The ratio of antiperspirant agent to surfactant is advantageously 1:1 to 30:1, preferably 2:1 to 20:1, very particular preferably 3:1 to 8:1.

With the product form of an aerosol spray the ratios relate to the active substance solution (without propellant gas).

If cationic as well as anionic surfactants are contained as charged surfactants according to the invention, the weight ratio between cationic and anionic surfactants is advantageously 10:1 to 1:3, preferably 6:1 to 1:2.

Preferably, the weight proportions of antiperspirant active substances, in particular aluminum chlorohydrate, are to be selected in the range of 1 to 25%, in particular 5 and 20% by weight.

Advantageously, cationic surfactants and anionic surfactants are then selected particularly in the ratio of 1:1.

It is interesting that through the addition of charged surfactants, in particular quaternary ammonium compounds, in particular of palmitamidopropyltrimonium chloride, to preparations comprising antiperspirants, in particular aluminum compounds staining of textiles is significantly reduced.

In particular quats with at least one long alkyl group have a function as detergent substance and are used, e.g., as cationic surfactants in products such as softeners. They can also have a disinfectant effect. Furthermore, quats are used in hair conditioners. They improve the physical properties such as combability, shine and antistatic behavior of the hair. As stated in the prior art on Varisoft® PATC, these substances allegedly prolong the retention of substances, such as dye in the hair.

According to the invention it has now surprisingly proven that the charged surfactants, such as quaternary ammonium compound, chiefly palmitamidopropyltrimonium chloride, improve the ability to wash out stains, which goes against the actual property of the quats according to the product information.

The use of the charged surfactants, in particular quaternary ammonium compounds, in cosmetic preparations to avoid or reduce the formation of stains caused by the cosmetic preparation in or on textiles as well as the improved ability to wash out these stains, in particular in cotton textiles, is thus predestined.

It is also surprising according to the invention that the use of quaternary ammonium compounds despite their electrolyte properties does not cause any stability problems and thus conventional formula systems can be used for the cosmetic preparations and antiperspirants.

The solubility thereof in the formula constituents present is to be taken into account in the incorporation of the charged surfactants.

Advantageously therefore a cosmetically acceptable solvent should be present, e.g., water, oils and alcohols. Guerbet alcohols, in particular octyldodecanol, are particularly preferred.

Thus an incorporation of, for example, Varisoft® PATC in W/O emulsions and anhydrous aerosols is easily possible if it is dissolved in octyldodecanol first.

A further essential aspect of the preparations according to the invention is their furthermore ensured skin tolerance, of which no loss need be feared due to the addition of charged surfactants, in particular the quaternary ammonium compounds.

In addition to the avoidance or reduction of staining in or on clothing, it was surprisingly also achieved that the stains that formed in clothing after washing, due the addition of charged surfactants in the preparation, seemed much lighter than without the addition of charged surfactants. As proof of the improved ability to be washed out and reduced staining, the following comparison tests were carried out in the form of test subject tests (panel).

Sequence of the tests:
Each test subject receives two identical products, which differ only in the addition of the charged surfactant (in this case: palmitamidopropyltrimonium chloride). One product is used under the left armpit, the other product under the right armpit.
The products are used during the entire test period.
Each test subject receives a white cotton T-shirt.
The T-shirt is worn for one day and subsequently washed and dried: washing conditions: 60° C. household washing machine, powder detergent
The washed T-shirts are tested photometrically for staining in the armpit region (determination of colorimetric measures in the CIE L*a*b color space)
The color values result form the difference in the values in the armpit region and the values of a reference area (unstained area e.g., shoulder or back)
In all at least 1 wear and wash cycle is carried out, preferably at least 3-6 wear and wash cycles are carried out Evaluation of the Color Values
dL value: white to gray; a negative value means a graying of the T-shirt
da value: red to green; a negative value means an intensification in the green range
db value: yellow to blue; a positive value means an intensification in the yellow range Composition of the Test Products

|  | Product without | Product with Palmitamidopropyltrimonium chloride |
|---|---|---|
| Aluminum chlorohydrate | 10.0 | 10.0 |
| Isoceteth-20 | 4.8 | 4.8 |
| Dicaprylylether | 3.0 | 3.0 |
| Glyceryl isostearate | 2.4 | 2.4 |
| PEG-150 Distearate | 0.7 | 0.7 |
| Butylene glycol | 3.0 | 3.0 |
| Varisoft ® PATC |  | 3.0 |
| Perfume | 1.0 | 1.0 |
| Water | 75.1 | 72.1 |
| Color values after 6 cycles |  |  |
| dL | −2.4 | −1.3 |
| da | −0.6 | −0.2 |
| db | 3.6 | 2.1 |

The comparison preparation without charged surfactant leads to a lower ability to be washed out, i.e., the stains compared to the product according to the invention were grayer (difference L value −1.1), greener (difference a value −0.4) and above all yellower (difference b value 1.5).

The color values were collected from all of the tests with all (7) test subjects and averaged.

Furthermore, the stains were visually evaluated. On a scale from 0 to 5 the test subjects evaluated the staining, how markedly the stain developed in the armpit region. A value of 0 means no stain, a value of 5 means a marked stain. The average stain intensity for a product without charged surfactant was evaluated at 3.7 and that with charged surfactant at 2.7.

FIG. 1 shows with the example of the b value (yellow) the difference for the formulations with and without charged surfactant for 7 individual test subjects after 6 wear and wash cycles. For all of the test subjects, the product according to the invention leads to less yellowing.

As proof of the improved ability to be washed out and reduced staining of the preparations according to the invention, further in vitro and in vivo tests were carried out.

In vitro Method for Determining Stain Intensity
Materials:
Textile: white, 100% cotton (jersey quality)
Test Substances/Media
 a.) Sebum: sebum according to BEY
 b.) Sweat: human sweat (artificial underarm sweat)
 c.) Comparison products
The application of sweat is optional.

Water quality: Tap water (preferably average hardness to hard)

Detergent: commercially available detergent, e.g., Spee Megaperls

Washing machine. Linitest+ from ATLAS

The sebum causes the stain to have a comparable yellow portion. Without sebum, the stains tend to be gray. A method of this type is already described in the literature: The Trouble with Stains, SPC July page 25-28; materials like sebum from BEY are available for example as standard test dirt from WfK-Testgewebe GmbH.

Application Quantities:
- a.) Preparation: 1 g on an area of 15 cm×2.5 cm of the textile, corresponds to 27 mg/cm$^2$
- b.) Human sweat: 0.5 g on an area of 15 cm×2.5 cm corresponds to 13 mg/cm$^2$
- c.) Sebum: 0.25 g on an area of 15 cm×2.5 cm corresponds to 7 mg/cm$^2$.

In further comparison tests, the application quantities can be selected in the following ranges in order to ensure a higher relation to practice, which, however, does not result in any significant changes in the results shown.

Product: Possible range: 10 mg/cm$^2$ to 50 mg/cm$^2$, preferably 13 mg/cm$^2$ to 40 mg/cm$^2$.

Sebum: Possible range: 2 mg/cm$^2$ to 15 mg/cm$^2$, preferably 5 mg/cm$^2$ to 10 mg/cm$^2$.

Human sweat: Possible range: 5 mg/cm$^2$ to 40 mg/cm$^2$, preferably 7 mg/cm$^2$ to 30 mg/cm$^2$.

Ratio product to sebum 1:1 to 7:1, preferably 2:1 to 5:1.

Ratio product to human sweat 1:3 to 7:1, preferably 1:1 to 4:1

Color Measurement:

Photometrically, determination of the colorimetric measures in the CIE L*a*b* color space Difference calculation compared to an unstained reference material Average from at least 5 measurements per area For evaluation the b value (yellow value) is preferably used Sequence:
1. Prewash and dry the textile sections
2. Mark the areas
3. Preferred application of the media in the following order: a.) preparation, b.) if applicable, sweat, c.) sebum, after each material wait at least 10 min until it has been absorbed.
   Alternatively, the substances can be mixed partially or completely with one another in advance and then applied in this mixture.
4. Store the samples at 38° C. and 80% relative humidity preferably for at least 12 hours
5. Wash the textile samples individually in the Linitest (e.g., 1 g powder detergent for 300 ml tap water, washing temperature 60° C.) and rinse in cold tap water
6. Dry at room temperature
7. Color measurement on the stained areas and an unstained reference area
8. Repeat the sequence from point 2 to 7 at least once, preferably 4 times The method for testing the stains caused in part by cosmetic or dermatological preparations containing antiperspirant substances on or in clothing is accordingly also according to the invention. Thereby
- a.) Preparation, in a quantity of 10 mg/cm$^2$ to 50 mg/cm$^2$,
- b.) If applicable, human sweat, in a quantity of 5 mg/cm$^2$ to 40 mg/cm$^2$ and
- c.) Sebum, in a quantity of 2 mg/cm$^2$ to 15 mg/cm$^2$ are successively applied to the same location on the clothing. Subsequently
  If applicable, the clothing is stored at 38° C. and 80% relative humidity preferably for at least 12 hours,
  The clothing is washed separately
  Optionally, rinsed with cold tap water
  Dried at room temperature and
the stained areas are measured photometrically against unstained reference areas of the same clothing by means of colorimetric measures in the CIE L*a*b color space In Vivo Method for Determining the Stain Intensity (as Described Above)

Materials:

Textile: White, 100% cotton, T-shirt

Detergent: commercially available detergent, Persil

Washing machine: commercially available model

Water quality: water of average hardness to hard

Color Measurement:

Photometrically, determination of the colorimetric measures in the CIE L*a*b color space.

Calculate difference compared to an unstained reference material, e.g., in the shoulder region of the T-shirt Average of at least 5 measurements per area For evaluation, the b value (yellow value) is preferably used Sequence:
1. Prewash the T-shirt
2. Distribute the product/the products (each product in succession or preferably a direct comparison of two products right armpit vs. left armpit are possible)
3. Product application at least 3 days for preconditioning
4. Wear the T-shirt after product application in the morning for at least 8 hours
5. Wash the T-shirt preferably at 60° C. (depending on the textile material)
6. Dry in a commercially available drier
7. Color measurement on the stained areas in the underarm area and an unstained reference area
8. Repetition of the sequence from point 4 through 7 at least 3 times Results of the In Vitro Tests (after 4 Cycles)

| Products as roller/ % by weight | Comparison 1 | P2 | P3 |
|---|---|---|---|
| Aluminum chlorohydrate | 10.0 | 10.0 | 10.0 |
| Isoceteth-20 | 4.8 | 4.8 | 4.8 |
| Dicaprylyl ether | 3.0 | 3.0 | 3.0 |
| Glyceryl isostearate | 2.4 | 2.4 | 2.4 |
| PEG-150 distearate | 0.7 | 0.7 | 0.7 |
| Butylene glycol | 3.0 | 3.0 | 3.0 |
| Varisoft ® PATC | | 3.0 | 3.0 |
| Plantapon LC7 | | | 1.0 |
| Water | 76.1 | 73.1 | 72.1 |
| b value | 8.1 | 5.1 | 3.6 |

| Products as roller/ % by weight | Comparison 2 | P4 | P5 |
|---|---|---|---|
| Aluminum chlorohydrate | 10.0 | 10.0 | 10.0 |
| Isoceteth-20 | 4.8 | 4.8 | 4.8 |
| Paraffinium liquidum | 3.0 | 3.0 | 3.0 |
| Glyceryl isostearate | 2.4 | 2.4 | 2.4 |
| Butylene glycol | 3.0 | 3.0 | 3.0 |
| PEG-150 distearate | 0.7 | 0.7 | 0.7 |
| Varisoft ® PATC | — | 1.0 | 2.0 |
| Plantapon LC7 | — | 1.0 | 1.0 |

-continued

| | | | |
|---|---|---|---|
| Perfume | 1.0 | 1.0 | 1.0 |
| Water | ad 100 | ad 100 | ad 100 |
| b value | 3.9 | 2.4 | 1.9 |

Varisoft ® PATC: 60% palmitamidopropyltrimonium chloride + 40% propylene glycol

| Products as sticks/% by weight | Comparison 3 | P6 |
|---|---|---|
| Aluminum zirconium tetrachlorohydrex GLY | 16.0 | 16.0 |
| Glyceryl stearate | 0.6 | 0.6 |
| Stearyl alcohol | 20.0 | 20.0 |
| Hydrogenated castor oil | 1.5 | 1.5 |
| PPG-14 Butylether | 15.0 | 15.0 |
| Cyclomethicone | 41.9 | 38.9 |
| Talc | 4.0 | 4.0 |
| Varisoft ® PATC | — | 3.0 |
| Perfume | 1.0 | 1.0 |
| b value | 7.2 | 4.9 |

| Products as sticks/% by weight | Comp. 4 | P7 | P8 | P9 |
|---|---|---|---|---|
| Aluminum zirconium tetrachlorohydrex GLY | 16 | 16 | 16 | 16 |
| Glyceryl stearate | 2 | 2 | 2 | 2 |
| Stearyl alcohol | 20 | 20 | 20 | 20 |
| Hydrogenated castor oil | 1.5 | 1.5 | 1.5 | 1.5 |
| Caprylic/capric triglycerides | 10 | 10 | 10 | 10 |
| Paraffinum liquidum | 12 | 12 | 12 | 12 |
| PPG-14 butyl ether | 20 | 19 | 18 | 18 |
| Cyclomethicone | 13.5 | 13.5 | 13.5 | 13.5 |
| Talc | 4 | 4 | 4 | 4 |
| Varisoft ® PATC | — | 1 | 1 | 1.5 |
| Plantapon LC 7 | — | — | 1 | 0.5 |
| Perfume | 1 | 1 | 1 | 1 |
| b value | 5.6 | 4.3 | 3.4 | 3.6 |

| Products as aerosols/% by weight | Comp. 5 | P10 |
|---|---|---|
| Aluminum chlorohydrate | 20 | 20 |
| Cetyl PEG/PPG-10/1 dimethicone | 1.5 | 3.0 |
| Polyglyceryl-2 dipolyhydroxystearate | 1.5 | — |
| Cyclomethicone | 11.75 | 11.75 |
| C12-15 Alkyl benzoate | 8 | 8 |
| Dicaprylyl ether | 6 | 6 |
| Octyldodecanol | 8 | 8 |
| Perfume | 3.5 | 3.5 |
| Varisoft ® PATC | — | 3.0 |
| Water | ad 100 | ad 100 |
| b value | 7.2 | 4.1 |

Aerosol % by weight based on emulsion, filling 30% by weight emulsion: 70% by weight propellant gas (mixture of propane, isobutane, butane)

Results of the In Vivo Tests:
10 Cycles, 26 Test Subjects:

| | Comp. 6 | P11 |
|---|---|---|
| Aluminum chlorohydrate | 10.0 | 10.0 |
| Isoceteth-20 | 4.8 | 4.8 |
| Dicaprylylether | 3.0 | 3.0 |
| Glyceryl isostearate | 2.4 | 2.4 |
| PEG-150 distearate | 0.7 | 0.7 |
| Butylene glycol | 3.0 | 3.0 |
| Varisoft ® PATC | | 3.0 |
| Plantapon LC 7 | | 1.0 |
| Perfume | 1.1 | 1.1 |
| Water | 75.0 | 71.0 |
| b value | 0.55 | 0.38 |

The comparison tests show that the preparations according to the invention P1-P11, comprising at least one charged surfactant, have a better ability to be washed out and reduced staining compared to preparations without these charged surfactants (Comp. 1 to Comp 6).

The comparison tests and the following examples impressively illustrate that the preparations according to the invention, in which the addition of charged surfactants leads to a reduction in staining in or on the clothing and in addition contributes to an improved ability of the stains to be washed out of the clothing.

Accordingly, the method for reducing or avoiding stains in or on clothing caused by the preparation is according to the invention, wherein the method comprises the steps:
topical application of a cosmetic or dermatological preparation comprising
one or more substances with antiperspirant effect and one or more charged surfactants
Wearing clothing over the topically applied skin areas and subsequently
Washing the clothing.

The compositions according to the invention can furthermore optionally contain additives customary in cosmetics, for example, perfume, thickeners, deodorants, antimicrobial substances, regreasing agents, complexing and masking agents, pearlescent agents, plant extracts, vitamins, active ingredients, preservatives, bactericides, dyes, pigments that have a coloring effect, thickeners, moisturizing and/or humectant substances, fats, oils, waxes or other usual constituents of a cosmetic or dermatological formulation, such as alcohols, polyols, polymers, foam stabilizers, electrolytes, organic solvents or silicone derivatives, unless they are counter to the composition according to the invention and the use thereof.

Moisturizers can also advantageously be used as anti-wrinkle substances for protection against aging of the skin, such as occur, e.g., in skin aging.

According to the invention, the formulations are advantageously macroscopically monophasic, based on the liquid portions of the formulation. That means: with the naked eye the liquids contained in the formula and optionally mixed with one another are discernible only as one phase at room temperature. Microscopically, that is, in the internal structure, however, more than one phase can be present, e.g., as in the case of an emulsion. Independent therefrom, preparations according to the invention can comprise solid substances, which optionally form a visible phase boundary to the monophasic liquid. This liquid/solid phase boundary counts as part of the monophasic nature according to the invention, since the monophasic nature relates to the liquid/liquid constituents. The macroscopically monophasic systems can thus contain particles (suspension).

In the form of an aerosol preparation, propellant gases possibly contained are not to be considered among the liquids, which can optionally form a phase boundary.

This monophasic nature is an essential distinguishing feature compared to the preparations of the prior art, such as are described, for example, in DE 10321138.

The feature "biphasic" therein means that the formulation has an aqueous phase and an oil phase, which at rest are present as two liquid layers separated by a phase boundary, but before use by shaking the container briefly can be mixed to form an oil-in-water emulsion or a water-in-oil emulsion. However, this mixing of the two phases is cancelled again quickly and as completely as possible as soon as the preparation is in the rest state. The time until complete demixing thereby lasts from a few seconds to 24 hours. The preparations according to the invention due to the monophasic quality have a more homogeneous distribution of the constituents containing them. This homogenous distribution is also decisive for example for the charged surfactants in the preparation for the stain reduction on or in the clothing thereof according to the invention.

A further essential distinguishing criterion with respect to DE 10321138 is that no nonionic surfactants and above all no emulsifiers are to be selected as charged surfactants according to the invention.

Preferred application forms of the preparation according to the invention are roll-on, stick form or the aerosol form. As propellant according to the invention preferably propane, propene, n-butane, iso-butane, iso-butene, n-pentane, pentene, iso-pentane, iso-pentene, methane, ethane, dimethyl ether, nitrogen, air, oxygen, nitrogen oxide, laughing gas, 1,1,1,3 tetrafluoroethane, heptafluoro-n-propane, perfluoroethane, monochlordifluoromethane, 1,1 difluoroethane and carbon dioxide are used individually or in combination. Propane, butane, iso-butane or mixtures of these propellant gases are particularly preferred.

The cited gases can be used for the purposes of the present invention in each case individually or in any mixtures with one another.

The numerical values are % by weight, based on the total mass of the preparation.

EXAMPLES

|  | Example 1 Atomizer | Example 2 Roller | Example 3 Roller |
|---|---|---|---|
| Aluminum chlorohydrate | 10.00 | 10.00 | 7.50 |
| Isoceteth-20 | 4.80 | 4.80 | — |
| Dicaprylyl ether | 3.00 | 3.00 |  |
| Glyceryl isostearate | 2.40 | 2.40 |  |
| PEG-150 Distearate |  |  | 0.70 |
| Butylene glycol | 3.00 |  |  |
| PPG-14 butylether |  |  | 3.50 |
| Diethylhexyl carbonate |  |  | 3.50 |
| Polyglyceryl-3 caprylate |  |  | 0.50 |
| Polyglyceryl-4 laurate |  |  | 0.25 |
| Methylglucose sesquistearate |  |  | 1.75 |
| Hydroxethylcellulose |  |  | 0.60 |
| Varisoft ® PATC | 3.00 | 3.00 | 3.00 |
| Perfume | 1.00 | 1.00 | 1.00 |
| Water | 72.80 | ad 100 | 77.40 |

|  | Example 4 Cream | Example 5 Stick |
|---|---|---|
| Aluminum zirconium tetrachlorohydrex GLY |  | 16.0 |
| Aluminum chlorohydrate | 10.0 |  |
| Water | 64.5 |  |
| Paraffinum liquidum | 5.0 |  |
| C13-16 Isoparaffin | 5.0 |  |
| PEG-40 Stearate | 3.5 |  |
| Trisodium EDTA | 1.5 |  |
| C12-15 Alkylbenzoate | 0.5 |  |
| Glyceryl stearate | 3.0 | 0.6 |
| Cetyl alcohol | 3.0 |  |
| Stearyl alcohol |  | 20.0 |
| Hydrogenated castor oil |  | 1.5 |
| PPG-14 Butylether |  | 15.0 |
| Cyclomethicone |  | 38.9 |
| Talc |  | 4.0 |
| Varisoft ® PATC | 3.0 | 3.0 |
| Perfume | 1.0 | 1.0 |

Varisoft ® PATC: 60% palmitamidopropyltrimonium chloride, 40% propylene glycol

|  | Example | | | |
|---|---|---|---|---|
| Roller | 6 | 7 | 8 | 9 |
| Aluminum chlorohydrate | 8.0 | 8.0 | 8.0 | 8.0 |
| Isoceteth-20 | 5.0 | 4.8 | 4.0 | 4.0 |
| Glyceryl isostearate | 2.2 | 2.4 | 2.0 | 2.0 |
| Dicaprylyl ether | — | 3.0 | — | — |
| Dicaprylal carbonate | — | — | — | 3.0 |
| Paraffinum liquidum | 3.0 | — | 3.0 | — |
| Octyldodecanol | — | — | 3.0 | 3.0 |
| Persea gratissima oil | 0.1 | 0.1 | 0.1 | 0.1 |
| Butylene glycol | 3.0 | 3.0 | — | — |
| Glycerin | — | — | 3.0 | 3.0 |
| PEG-150 Distearate | 0.7 | 0.7 | 0.7 | 0.7 |
| Palmitamidopropyltrimonium chloride + propylene glycol (Varisoft ® PATC) | 1.0 | 1.0 | 1.0 | 1.0 |
| Laureth-7 citrate (Plantapon LC 7) | 1.0 | 1.0 | 1.0 | 1.0 |
| Perfume | 1.0 | 1.0 | 1.0 | 1.0 |
| Water | ad 100 | ad 100 | ad 100 | ad 100 |

|  | example | |
|---|---|---|
| Roller | 10 | 11 |
| Trisodium EDTA | 1.5 | 1.5 |
| Steareth-21 | 1.5 | 1.0 |
| Steareth-2 | 2.5 | 2.0 |
| PPG-15 Stearyl ether | 3.0 | 3.0 |
| Aluminum chlorohydrate | 10.0 | 10.0 |
| Plantapon LC 7 | 2.5 |  |
| TEGO Care CE 40 |  | 3.0 |
| Aqua | ad 100 | ad 100 |

TEGO Care CE 40: 40% palmitamidopropyltrimonium chloride + 70% cetearyl alcohol

|  | example | | |
|---|---|---|---|
| Aerosols | 12 | 13 | 14 |
| Aluminum chlorohydrate | 35.00 | 35.00 | 35.00 |
| Octyldodecanol | 12.00 | 12.00 | 12.00 |
| Disteardimonium hectorite | 4.00 | 4.00 | 4.00 |
| Varisoft ® PATC | 3.00 |  |  |
| TEGO Care CE 40 |  | 3.00 |  |
| Plantapon LC 7 |  |  | 3.00 |
| Perfume | 6.25 | 6.25 | 6.25 |
| Cyclomethicone | ad 100 | ad 100 | ad 100 |

What is claimed is:

1. A method of reducing or avoiding staining in or on clothing caused by a cosmetic or dermatological preparation in the form of at least one of an oil-in-water emulsion, a water-in-oil emulsion, a suspension, and an anhydrous preparation which has come into contact with the clothing and comprises one or more antiperspirant substances and/or of improving the ability of stains in or on clothing which are caused at least in part by said preparation which has come into contact with the clothing to be washed out from the clothing, wherein the method comprises including in the preparation, prior to contact thereof with the clothing, one or more charged surfactants which comprise one or more cationic surfactants comprising at least one quaternary ammonium compound of formula (I):

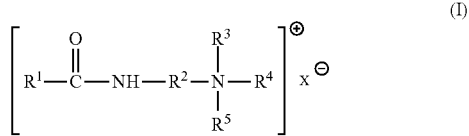

wherein:
R¹ represents a saturated or unsaturated linear, branched or cyclic alkyl group or an aryl group having from 8 to 24 carbon atoms,
R² represents a saturated or unsaturated, linear, branched, or cyclic, substituted or un-substituted alkylene group having from 1 to 10 carbon atoms and from 0 to 5 hydroxy groups,
$R^3$, $R^4$, $R^5$ independently of one another represent hydrogen, a $C_1$-$C_4$ alkyl group, a $C_5$ or $C_6$ cycloalkyl group, an aryl group or a $C_2$-$C_4$ hydroxyalkyl group, and
X represents a monovalent anion;
in an amount which is sufficient for reducing or avoiding staining in or on the clothing caused by the preparation and/or for improving the ability of stains in or on the clothing caused by the preparation to be washed out from the clothing.

2. The method of claim 1, wherein after washing the clothing at least once, stains in the clothing which are caused by the preparation have a b value in the CIE L*a*b color space that is lower than a b value before washing.

3. The method of claim 1, wherein $R^1$ in formula (I) represents a saturated linear $C_{10}$-$C_{18}$ alkyl group.

4. The method of claim 3, wherein $R^2$ in formula (I) represents —CH₂CH₂CH₂—.

5. The method of claim 1, wherein the at least one quaternary ammonium compound comprises one or more of palmitamidopropyltrimonium chloride, behenamidopropyl ethyldimonium ethosulfate, stearamidopropyl trimonium methosulfate, and undecylamidopropyltrimonium methosulfate.

6. The method of claim 1, wherein the at least one quaternary ammonium compound comprises palmitamidopropyltrimonium chloride.

7. The method of claim 1, wherein the method further comprises including in the preparation, before contact with the clothing, at least one anionic surfactant.

8. The method of claim 7, wherein the at least one anionic surfactant comprises laureth-7 citrate.

9. The method of claim 7, wherein a weight ratio of the one or more cationic surfactants to the at least one anionic surfactant is from 10:1 to 1:3.

10. The method of claim 9, wherein the weight ratio is from 6:1 to 1:2.

11. The method of claim 1, wherein from 0.1% to 5% by weight of the one or more quaternary ammonium compounds are included, based on a total weight of the preparation.

12. The method of claim 1, wherein the preparation is present as an aerosol spray.

13. The method of claim 1, wherein the preparation is anhydrous.

14. The method of claim 1, wherein the preparation is present as a roll-on.

15. The method of claim 1, wherein the preparation is present as a stick.

16. The method of claim 1, wherein the preparation is present as a cream.

17. The method of claim 1, wherein the preparation is present as a water-in-oil emulsion or oil-in-water emulsion.

18. A method of reducing or avoiding staining in or on clothing caused by a cosmetic or dermatological preparation which has come into contact with the clothing and comprises one or more antiperspirant substances and/or of improving the ability of stains in or on clothing which are caused at least in part by said preparation which has come into contact with the clothing to be washed out from the clothing, wherein the method comprises including in the preparation, prior to contact thereof with the clothing, one or more charged surfactants which include palmitamidopropyltrimonium chloride and at least one anionic surfactant in amounts which are sufficient for reducing or avoiding staining in or on the clothing caused by the preparation and/or for improving the ability of stains in or on the clothing caused by the preparation to be washed out from the clothing, the preparation being in the form of at least one of an oil-in-water emulsion, a water-in-oil emulsion, a suspension, and an anhydrous preparation.

* * * * *